(12) United States Patent
Miura et al.

(10) Patent No.: US 7,612,007 B2
(45) Date of Patent: Nov. 3, 2009

(54) PROCESS FOR REGENERATING CATALYST

(75) Inventors: Naoki Miura, Niihama (JP); Koichi Nagai, Niihama (JP); Noriaki Suyasu, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 306 days.

(21) Appl. No.: 11/819,463

(22) Filed: Jun. 27, 2007

(65) Prior Publication Data

US 2008/0004173 A1 Jan. 3, 2008

(30) Foreign Application Priority Data

Jun. 28, 2006 (JP) .......................... P2006-177871

(51) Int. Cl.
*B01J 38/12* (2006.01)
(52) U.S. Cl. .............................. 502/38; 502/53; 502/54
(58) Field of Classification Search ................... 502/38, 502/53, 54
See application file for complete search history.

(56) References Cited

U.S. PATENT DOCUMENTS 4,425,255 A 1/1984 Toyoda et al.
4,871,700 A 10/1989 Uchida et al.
2005/0096487 A1 5/2005 Dieterle et al.

FOREIGN PATENT DOCUMENTS

| EP | 0 102 641 A2 | 3/1984 |
|----|----|----|
| EP | 0 169 449 A2 | 1/1986 |
| EP | 0 339 119 A1 | 2/1989 |
| JP | 60-163830 A | 8/1985 |
| JP | 63-137755 A | 6/1988 |
| JP | 5-184945 A | 7/1993 |
| JP | 2000-288396 A | 10/2000 |

*Primary Examiner*—Edward M Johnson
(74) *Attorney, Agent, or Firm*—Birch, Stewart, Kolasch & Birch, LLP

(57) ABSTRACT

A process for regenerating a catalyst consisting of a mixed oxide having molybdenum, bismuth and iron used for preparing an unsaturated aldehyde and/or an unsaturated carboxylic acid by catalytically oxidizing propylene, isobutylene and/or tert.-butanol with molecular oxygen in a gas phase, in which the catalyst is regenerated by thermally treating the deteriorated catalyst in an atmosphere of a gas containing molecular oxygen at a temperature of 200 to 500° C., and then thermally treating the catalyst in the presence of a reducing compound at a temperature of 200 to 500° C.

3 Claims, No Drawings

US 7,612,007 B2

PROCESS FOR REGENERATING CATALYST

FIELD OF THE INVENTION

The present invention relates to a process for regenerating a catalyst used for preparing an unsaturated aldehyde and/or an unsaturated carboxylic acid by catalytically oxidizing a compound selected from propylene, isobutylene and tert.-butanol with molecular oxygen in a gas phase. The present invention also relates to a process for preparing an unsaturated aldehyde and/or an unsaturated carboxylic acid using a catalyst which is regenerated by such a regeneration process.

BACKGROUND ART

Hitherto, a so-called molybdenum-bismuth-iron mixed oxide catalyst is used for preparing unsaturated aldehydes and/or unsaturated carboxylic acids by a gas phase catalytic oxidation reaction of a corresponding raw material compound. However, the catalytic activity of the catalyst decreases when the catalyst is used for the oxidation reaction for a long time or when it receives excessive thermal load. Therefore, it is highly desired to provide a process for restoring the once decreased catalytic activity of such a catalyst to regenerate the catalyst which can be well used in the catalytic oxidation reaction.

As a process for regenerating a catalyst used for preparing unsaturated aldehydes and/or unsaturated carboxylic acids, EP 0 169 449 A2, EP 0 339 119 A1 and JP 05-184945 A disclose processes comprising thermally treating deteriorated catalysts in an atmosphere of a gas containing molecular oxygen, and U.S. Pat. No. 4,425,255 discloses a process comprising thermally treating a deteriorated catalyst in an atmosphere of a reducing gas at a temperature of 200 to 700° C. and then thermally treating the catalyst in an atmosphere of a gas containing molecular oxygen at a temperature of 550 to 700° C.

However, the catalysts which are regenerated by the above processes tend to have an excessively high oxidizing ability on raw material compounds, and to have lowered selectivities. In addition, the duration of the catalytic activities of such catalysts is shortened and the catalysts should be regenerated at short intervals. Therefore, the processes of the prior art are not always satisfactory.

SUMMARY OF THE INVENTION

An object of the present invention is to provide a process for regenerating a catalyst for catalytically oxidizing a raw material compound to prepare an unsaturated aldehyde and/or an unsaturated carboxylic acid, so that the regenerated catalyst does not induce an excessive oxidation reaction, and has a good selectivity and a longer duration of a catalytic activity.

According to one aspect, the present invention provides a process for regenerating a catalyst consisting of a mixed oxide comprising molybdenum, bismuth and iron, which is used for preparing an unsaturated aldehyde and/or an unsaturated carboxylic acid by catalytically oxidizing at least one compound selected from the group consisting of propylene, isobutylene and tert.-butanol with molecular oxygen in a gas phase, which process comprises the steps of:

thermally treating the deteriorated catalyst having a decreased catalytic activity in an atmosphere of a gas containing molecular oxygen at a temperature of 200 to 500° C., and then thermally treating the catalyst in the presence of a reducing compound at a temperature of 200 to 500° C.

According to another aspect, the present invention provides a process for preparing an unsaturated aldehyde and/or an unsaturated carboxylic acid comprising the step of: catalytically oxidizing at least one compound selected from the group consisting of propylene, isobutylene and tert.-butanol with molecular oxygen in a gas phase in the presence of a catalyst which is regenerated by the regeneration process according to the present invention.

According to the present invention, a catalyst for preparing an unsaturated aldehyde and/or an unsaturated carboxylic acid, which has a good selectivity and a long duration of a catalytic activity, can be regenerated, and an unsaturated aldehyde and/or an unsaturated carboxylic acid can be prepared at high yields using such a regenerated catalyst.

DETAILED DESCRIPTION OF THE PREFERRED EMBODIMENTS

A catalyst to be regenerated by the process of the present invention may be a conventional catalyst for preparing an unsaturated aldehyde and/or an unsaturated carboxylic acid by catalytically oxidizing at least one compound selected from the group consisting of propylene, isobutylene and tert.-butanol with molecular oxygen in a gas phase, and generally consists of a mixed oxide comprising molybdenum, bismuth and iron. Such a catalyst may be prepared by a conventional method, which is disclosed by EP 0 102 641 A2, JP 60-163830 A, JP 2000-288396 A, etc.

The catalytic activity of the catalyst may decrease, when the catalyst is used for a long time in the gas-phase catalytic oxidation reaction or when it receives excessive heat load. The process of the present invention regenerates the catalyst having a decreased catalytic activity by heating it at a specific temperature in an atmosphere of a gas containing molecular oxygen, and then heating it in the presence of a reducing compound to restore the catalytic activity of the catalyst for preparing an unsaturated aldehyde and/or an unsaturated carboxylic acid. In particular, the regeneration process of the present invention is preferably employed to regenerate the deteriorated catalyst the catalytic activity of which is decreased by the prolonged use in the oxidation reaction.

In the regeneration process of the present invention, the concentration of molecular oxygen in the atmospheric gas is usually from 1 to 30% by volume, preferably from 10 to 25% by volume. As the molecular oxygen, an air or pure oxygen may be used. The molecular oxygen may optionally be diluted with nitrogen, carbon dioxide, water, helium, argon, etc. Among them, an air is advantageously used from the economical viewpoint.

The heat treatment in the atmosphere of a gas containing molecular oxygen is usually carried out at a temperature of from 200 to 500° C., preferably from 200 to 400° C. When the temperature is lower than 200° C., the catalyst may not be sufficiently regenerated. When the temperature exceeds 500° C., the catalyst tends to be sintered. In general, the heat treatment is carried out for 1 to 40 hours.

After the heat treatment of the catalyst with molecular oxygen, the catalyst is further heated in the presence of a reducing compound. Hereinafter, this heating of the catalyst in the presence of a reducing compound may be simply referred to as "reduction treatment".

The combination of the heat treatments described above can regenerate the catalyst so that it attains a high selectivity and has a long duration of a catalytic activity.

Examples of the reducing compound include hydrogen, ammonia, carbon monoxide, hydrocarbons, alcohols, aldehydes, amines, etc. They may optionally be used as a mixture of two or more of them. Preferably, each of the hydrocarbons, alcohols, aldehydes and amines has 1 to about 6 carbon atoms. Specific examples of such hydrocarbons include saturated aliphatic hydrocarbons such as methane, ethane, propane, n-butane, isobutane, etc.; unsaturated aliphatic hydrocarbons such as ethylene, propylene, α-butylene, β-butylene, isobutylene, etc.; benzene; and the like. Specific examples of such alcohols include saturated aliphatic alcohols such as methanol, ethanol, n-propanol, isopropanol, n-butanol, isobutanol, sec.-butanol, tert.-butanol, etc.; unsaturated aliphatic alcohols such as allyl alcohol, crotyl alcohol, methallyl alcohol, etc.; and phenol. Specific examples of such aldehydes include saturated aliphatic aldehydes such as formaldehyde, acetaldehyde, propionaldehyde, n-butylaldehyde, isobutylaldehyde, etc.; and unsaturated aliphatic aldehydes such as acrolein, crotonaldehyde, methacrolein, etc. Specific examples of such amines include saturated aliphatic amines such as methylamine, dimethlamine, trimethylamine, ethylamine, diethylamine, triethylamine, etc.; unsaturated aliphatic amines such as allylamine, diallylamine, etc.; and aniline.

The reduction treatment is carried out by heating the catalyst in a gas containing the above reducing compound. The concentration of the reducing compound in the gas is usually from 0.1 to 50% by volume, preferably from 0.1 to 30% by volume. The reducing compound is diluted with nitrogen, carbon dioxide, water, helium, argon, etc. to attain such a concentration. The molecular oxygen may be present in such an amount that the effect of the reduction of the catalyst is not impaired. Preferably, the molecular oxygen is not present.

A temperature in the reduction treatment is usually from 200 to 500° C., preferably 250 to 450° C., more preferably 300 to 400° C. When the reduction temperature is lower than 200° C., the catalyst may not be sufficiently regenerated. When the temperature exceeds 500° C., the catalytic activity or the duration of the catalytic activity of the catalyst tend to be decreased. The reduction treatment time is usually from 1 minute to 20 hours, preferably from 10 minutes to 10 hours.

The heat treatment of the catalyst in the atmosphere of a gas containing molecular oxygen and the reduction treatment of the catalyst may be carried out using a conventional calcination (or firing) furnace, for example, a multistage calcination furnace, a continuous calcination furnace such as a roller-hearth kiln, a drum type calcination furnace, etc. When the catalyst having the decreased catalytic activity after being used for the gas-phase catalytic oxidation is subjected to the heat treatment in the atmosphere of a gas containing molecular oxygen and the reduction treatment, it is removed from a reactor for the catalytic oxidation and transferred to the separate calcination furnace and then the heat treatment in the atmosphere of a gas containing molecular oxygen and the reduction treatment of the catalyst are carried out. Alternatively, the catalyst having the decreased catalytic activity is subjected to the heat treatment in the atmosphere of a gas containing molecular oxygen and the reduction treatment in the reactor for the catalytic oxidation. The latter is advantageous from the economical viewpoint.

The gas containing molecular oxygen or the gas containing the reducing compound may be intermittently or continuously supplied to the furnace. Furthermore, these gases may be passed through the furnace, and the exhaust gas from the furnace may be recycled to the furnace, if necessary.

The catalyst which is regenerated according to the present invention has good catalytic properties, such as a good selectivity and a prolonged duration of a catalytic activity. When propylene is catalytically oxidized in the presence of the regenerated catalyst, acrolein and/or acrylic acid can be prepared in high yields, while when isobutylene or tert.-butanol is catalytically oxidized in the presence of the regenerated catalyst, methacrolein and/or methacrylic acid can be prepared in high yields.

In the catalytic oxidation, a mixture of the unsaturated aldehyde and the unsaturated carboxylic acid is obtained. When the oxidation reaction is carried out while keeping a conversion of a raw material compound low, the unsaturated aldehyde can selectively be prepared.

In general, the gas-phase catalytic oxidation is carried out by supplying at least one compound selected from the group consisting of propylene, isobutylene and tert.-butanol together with molecular oxygen to a fixed bed multitubular reactor packed with the catalyst, while it may be carried out using a fluidized bed reactor or a moving bed reactor. As the molecular oxygen, an air is usually used. Apart from the raw material compound and the molecular oxygen, the raw material gas may optionally contain other gaseous material such as nitrogen, carbon dioxide, carbon monoxide, steam, etc.

The reaction temperature is usually from 250 to 400° C. The reaction pressure is usually from an atmospheric pressure to 500 kPa, although a reduced pressure may be used. A molar ratio of the molecular oxygen to the raw material compound is usually from 1:1 to 3:1. The space velocity of the raw material gas is usually from 500 to 5,000 hr$^{-1}$ at a standard temperature and pressure (STP).

The present invention will be illustrated by the following Examples, which do not limit the scope of the present invention in any way. Unless otherwise indicated, the volumes of gasses and a space velocity are those at STP. In the following Examples, a conversion (%), a total selectivity and a total yield (%) are defined as follows:

Conversion (%)=100×[(Moles of supplied isobutylene)−(Moles of unreacted isobutylene)]/(Moles of supplied isobutylene)

Total selectivity (%) 100×[Total moles of methacrolein and methacrylic acid]/[(Moles of supplied isobutylene)−(Moles of unreacted isobutylene)]

Total yield (%)=100×[Total moles of methacrolein and methacrylic acid]/Moles of supplied isobutylene)

REFERENCE EXAMPLE 1

(a) Preparation of Fresh Catalyst A

Ammonium molybdate [$(NH_4)_6Mo_7O_{24}.4H_2O$] (13,241 g) was dissolved in warm water (15,000 g). This solution is referred to as "Solution A". Separately, iron(III) nitrate [$Fe(NO_3)_3.9H_2O$] (6,060 g), cobalt nitrate [$Co(NO_3)_3.6H_2O$] (13,096 g) and cesium nitrate [$CsNO_3$] (585 g) were dissolved in warm water (6,000 g), and then bismuth nitrate [$Bi(NO_3)_3.5H_2O$] (2,910 g) was dissolved. This solution is referred to as "Solution B". Solution B was poured in Solution A while stirring to obtain a slurry. Then, the slurry was spray dried to obtain a dried material. To 100 parts by weight of the dried material, 2.54 parts by weight of antimony trioxide ($Sb_2O_3$) and 6 parts by weight of silica-alumina fiber (RFC 400-SL manufactured by SAINT-GOBAIN™) were added, and the mixture was molded in the form of rings each having an outer diameter of 6.0 mm, an inner diameter of 2.0 mm and a length of 6 mm, and calcined in an air stream at 543° C. for 6 hours to obtain Fresh Catalyst A. This catalyst had an atomic composition (except oxygen) of $Mo_{12}Bi_{0.96}Sb_{0.48}Fe_{2.4}Co_{7.2}Cs_{0.48}Si_{1.43}Al_{1.55}$.

(b) Oxidation Reaction Using Fresh Catalyst A

Fresh Catalyst A (1 ml) prepared in the previous step (a) was diluted with silicon carbide which is inert to the oxidation reaction and packed in a glass reactor tube having an inner diameter of 18 mm. Then, a mixed gas of isobutylene, oxygen, nitrogen and steam in a molar ratio of 1.0:2.2:6.2:2.0 was supplied in the reactor tube at a space velocity of 5,250 hr$^{-1}$, which is slightly higher than a usually space velocity, to catalytically oxidize isobutylene at a reaction temperature of 410° C. After one day from the start of the oxidation reaction, the conversion of isobutylene was 47.5%, and the total selectivity of methacrolein and methacrylic acid was 83.7%. After 42 days from the start of the oxidation reaction, the conversion of isobutylene was 36.4%, and the total selectivity of methacrolein and methacrylic acid was 87.4%.

COMPARATIVE EXAMPLE 1

(a) Regeneration (1) (Heat Treatment with Air Only)

The oxidation reaction in the step (b) of Reference Example 1 was terminated when 42 days lapsed from the start of the oxidation reaction. Then, an air was supplied in the reactor tube at a space velocity of 915 hr$^{-1}$ at 370° C. for 20 hours to heat treat the catalyst.

(b) Oxidation Reaction after Regeneration of Catalyst

After regenerating the catalyst in the previous step (a), the oxidation reaction was restarted. The performances of the reaction were evaluated after 1 day and 15 days from the restart of the reaction. The results are shown in Table 1.

EXAMPLE 1

(a) Regeneration (2) (Heat Treatment with Air Followed by Reduction Treatment)

After carrying out the oxidation reaction for 15 days in the step (b) of Comparative Example 1, an air was supplied in the reactor tube at a space velocity of 915 hr$^{-1}$ at 370° C. for 20 hours to heat treat the catalyst. Then, the mixed gas of 0.5% by volume of isobutylene and 99.5% by volume of nitrogen was supplied in the reactor tube at a space velocity of 600 hr$^{-1}$ at 350° C. for 5 hours to reduce the catalyst.

(b) Oxidation Reaction After Regeneration of Catalyst

After regenerating the catalyst in the previous step (a), the oxidation reaction was restarted. The performances of the reaction were evaluated after 1 day and 16 days from the restart of the reaction. The results are shown in Table 1.

REFERENCE EXAMPLE 2

(a) Preparation of Fresh Catalyst B

Fresh Catalyst B was prepared in the same manner as in the step (a) of Reference Example 1 except that no antimony trioxide was used during the molding of the catalyst, and the calcination temperature was changed to 519° C. This catalyst had an atomic composition (except oxygen) of $Mo_{12}Bi_{0.96}Fe_{2.4}Co_{7.2}Cs_{0.48}Si_{1.43}Al_{1.55}$.

(b) Oxidation Reaction Using Fresh Catalyst B

Fresh Catalyst A (692 ml) was packed in an inlet region of a stainless steel reactor tube having an inner diameter of 25.4 mm, while Fresh Catalyst B (692 ml) was packed in an outlet region of the reactor tube. Then, a mixed gas of isobutylene, oxygen, nitrogen and steam in a molar ratio of 5.2:12.4:75.3:7.1 was supplied in the reactor tube at a space velocity of 1,290 hr$^{-1}$ to catalytically oxidize isobutylene while controlling a reaction temperature so that the conversion of isobutylene was maintained around 99%. After 24 hours from the start of the oxidation reaction, the performances of the reaction were evaluated. At a reaction temperature of 360° C., the conversion of isobutylene was 98.8%, the total selectivity of methacrolein and methacrylic acid was 84.8%, and the total yield of methacrolein and methacrylic acid was 83.8%. After 6,300 hours from the start of the oxidation reaction, the performances of the reaction were again evaluated. At a reaction temperature of 368° C., the conversion of isobutylene was 99.1%, the total selectivity of methacrolein and methacrylic acid was 85.4%, and the total yield of methacrolein and methacrylic acid was 84.6%.

COMPARATIVE EXAMPLE 2

(a) Regeneration (3) (Heat Treatment with Air Only)

The oxidation reaction in the step (b) of Reference Example 2 was terminated when 6,300 hours lapsed from the start of the oxidation reaction. Then, an air was supplied in the reactor tube at a space velocity of 915 hr$^{-1}$ at 370° C. for 20 hours to heat treat the catalyst.

(b) Oxidation Reaction After Regeneration of Catalyst

After regenerating the catalyst in the previous step (a), the oxidation reaction was restarted. The performances of the reaction were evaluated after 100 hours, 1,000 hours and 4,300 hours from the restart of the reaction. The results are shown in Table 2.

EXAMPLE 2

(a) Regeneration (4) (heat Treatment with Air Followed by Reduction Treatment)

After carrying out the oxidation reaction for 4,300 hours in the step (b) of Comparative Example 2, an air was supplied in the reactor tube at a space velocity of 915 hr$^{-1}$ at 370° C. for 20 hours to heat treat the catalyst. Then, the mixed gas of 0.5% by volume of isobutylene and 99.5% by volume of nitrogen was supplied in the reactor tube at a space velocity of 74 hr$^{-1}$ at 360° C. for 8 hours to reduce the catalyst.

(b) Oxidation Reaction After Regeneration of Catalyst

After regenerating the catalyst in the previous step (a), the oxidation reaction was restarted. The performances of the reaction were evaluated after 100 hours, 1,000 hours and 4,300 hours from the restart of the reaction. The results are shown in Table 2.

TABLE 1

| | Regeneration Treatment | Reaction time | Reaction temperature (° C.) | Conversion (%) | Total selectivity (%) |
|---|---|---|---|---|---|
| Ref. Ex. 1 | None (with fresh catalyst) | 1 day 42 days | 410 410 | 47.5 36.4 | 83.7 87.4 |
| Comp. Ex. 1 | Heat treatment with air | 1 day 15 days | 410 410 | 43.6 31.6 | 86.9 86.6 |
| Example 1 | Heat treatment with air followed by reduction treatment | 1 day 16 days | 410 410 | 44.1 38.0 | 86.9 87.0 |

Comparing the results of Comparative Example 1 in which the catalyst was regenerated by the heat treatment with air only, with those of Example 1 in which the catalyst was regenerated by the heat treatment with air and the subsequent reduction treatment, the conversion was recovered after 1 day from the restart of the oxidation reaction in both cases. However, the duration of the conversion achieved by the catalyst which was regenerated by the heat treatment with air only was not sufficient. The prolonged duration of the conversion was achieved by the catalyst which was regenerated by the heat treatment with air and the subsequent reduction treatment according to the present invention.

TABLE 2

|  | Regeneration treatment | Reaction time | Reaction temperature (° C.) | Conversion (%) | Total selectivity (%) | Total yield (%) |
|---|---|---|---|---|---|---|
| Ref. Ex. 2 | None (with fresh catalyst) | 24 hours | 360 | 98.8 | 84.8 | 83.8 |
|  |  | 6,300 hours | 368 | 99.1 | 85.4 | 84.6 |
| Comp. Ex. 2 | Heat treatment with air | 100 hours | 342 | 99.4 | 83.1 | 82.6 |
|  |  | 1,000 hours | 351 | 99.3 | 85.3 | 84.7 |
|  |  | 4,300 hours | 370 | 97.6 | 87.3 | 85.2 |
| Example 2 | Heat treatment with air followed by reduction treatment | 100 hours | 349 | 99.4 | 86.1 | 85.6 |
|  |  | 1,000 hours | 343 | 99.2 | 86.5 | 85.8 |
|  |  | 4,300 hours | 350 | 99.2 | 86.4 | 85.7 |

In Comparative Example 2 in which the catalyst was regenerated by the heat treatment with air only, the reaction temperature should have been gradually increased as the oxidation reaction proceeded so as to attain an intended conversion of around 99%. After 4,300 hours from the restart of the oxidation reaction, a conversion of around 99% could not be attained even when the reaction temperature was raised to 370° C. In contrast, in Example 2 in which the catalyst was regenerated by the heat treatment with air and the subsequent reduction treatment, the intended conversion could be attained without raising the reaction temperature, as the reaction proceeded. That is, the regenerated catalyst had the prolonged duration of the catalytic activity. Furthermore, the total yield was high.

What is claimed is:

1. A process for regenerating a catalyst consisting of a mixed oxide comprising molybdenum, bismuth and iron, which is used for preparing an unsaturated aldehyde and/or an unsaturated carboxylic acid by catalytically oxidizing at least one compound selected from the group consisting of propylene, isobutylene and tert.-butanol with molecular oxygen in a gas phase, which process comprises the steps of:

thermally treating the deteriorated catalyst having a decreased catalytic activity in an atmosphere of a gas containing molecular oxygen at a temperature of 200 to 500° C., and then thermally treating the catalyst in the presence of a reducing compound at a temperature of 200 to 500° C.

2. The process according to claim 1, wherein said reducing compound is at least one compound selected from the group consisting of hydrogen, ammonia, carbon monoxide, hydrocarbons having 1 to 6 carbon atoms, alcohols having 1 to 6 carbon atoms, aldehydes having 1 to 6 carbon atoms and amines having 1 to 6 carbon atoms.

3. A process for preparing an unsaturated aldehyde and/or an unsaturated carboxylic acid comprising the step of:

catalytically oxidizing at least one compound selected from the group consisting of propylene, isobutylene and tert.-butanol with molecular oxygen in a gas phase in the presence of a catalyst which is regenerated by a process for regenerating a catalyst according to claim 1.

* * * * *